US00PP09103P

United States Patent [19]

Wandell

[11] Patent Number: Plant 9,103

[45] Date of Patent: Apr. 11, 1995

[54] OAK TREE 'CRIMSCHMIDT'

[75] Inventor: Willet N. Wandell, Oquawka, Ill.

[73] Assignee: J. Frank Schmidt & Son Co., Boring, Oreg.

[21] Appl. No.: 236,740

[22] Filed: May 2, 1994

[51] Int. Cl.[6] ..... A01H 5/00

[52] U.S. Cl. ..... Plt./53.7

[58] Field of Search ..... Plt. 53.7

*Primary Examiner*—James R. Feyrer

*Attorney, Agent, or Firm*—Klarquist Sparkman Campbell Leigh & Whinston

[57] ABSTRACT

A new variety of Oak tree, which is named 'Crimschmidt', has a narrow fastigiate growth habit, a red fall color and demonstrated resistance to powdery mildew.

1 Drawing Sheet

DESCRIPTION

The present invention relates to a new and distinct variety of oak tree which is named 'Crimschmidt'.

I discovered my new tree as a chance seedling growing in a row of *Quercus robur* seedings in a cultivated area of my nursery in Oquawka, Ill. I had collected the seed from a group of *Quercus robur* trees growing in a cultivated area in Champaign, Ill. *Quercus alba* trees were growing in the vicinity of my seed trees. None of their seed were included in the *Quercus robur* seed I collected, however, a *Quercus alba* tree may have served as a pollen parent for my new tree, which has a hybrid appearance.

In examining this row of *Quercus robur* seedlings in my Oquawka, Ill. nursery, my attention was particularly drawn to my new tree because it displayed the columnar growth habit typically found in *Quercus robur* fastigiata in combination with a red fall color which is completely atypical of *Quercus robur*. On further examination, I noticed that the foliage of my new tree had a particularly high quality appearance and was lacking any infection from powdery mildew, a foliage disease present on almost all *Quercus robur* trees in the nursery.

I observed this tree for a period of time and became quite convinced it would be a valuable new tree for landscape use because it combined a narrow fastigiate growth habit with red fall color and demonstrated resistance to powdery mildew.

Asexual propagation of my new tree was then performed at my direction at the J. Frank Schmidt and Son Co. nursery in Boring, Oreg., by budding onto *Quercus robur* seedlings.

This propagation, and successive asexual propagation by budding, and observation of the resulting progeny, has proven the characteristics of my new variety of tree to be firmly fixed. Furthermore, these observations have confirmed that my new variety represents a new and improved variety of oak tree, as particularly evidenced by the unique combination of a narrow fastigiate growth, red fall color, and a greater degree of resistance to powdery mildew than is typical of the species.

I do not know of any other oak tree cultivar which combines a fastigiate growth form with red fall color.

The accompanying photographs depict the color of the tree and foliage of my new variety, as well as the shape of the tree, as nearly true as is reasonably possible to make the same in a color illustration of this character.

Figure 1:
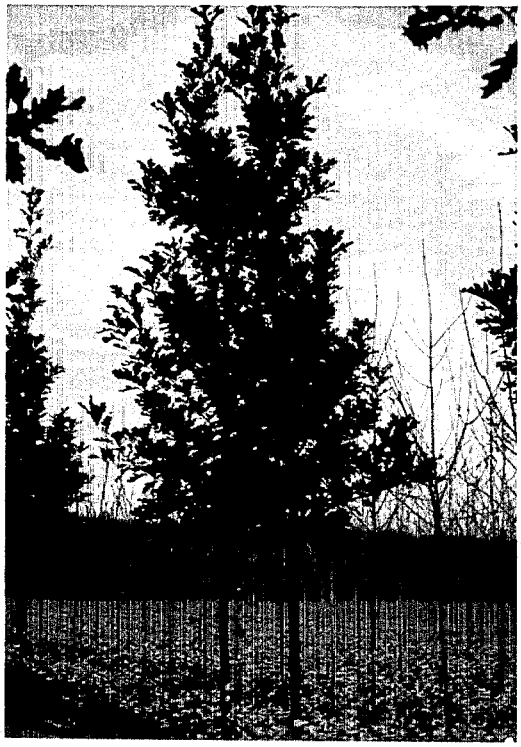
FIG. 1 is a color photograph of two trees of the present invention.
Figure 2:
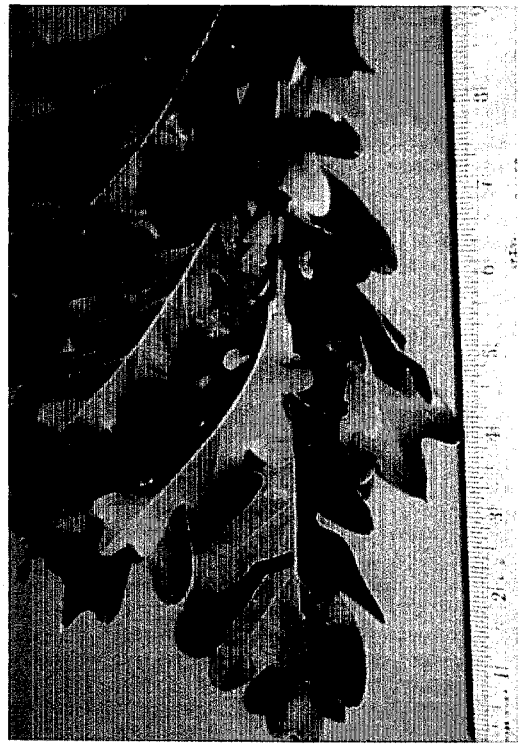
FIG. 2 is a color photograph of leaves of the tree of the present invention; and, FIG. 3 is a color photograph of leaves of the tree of the present invention in their fall color.
Figure 3:
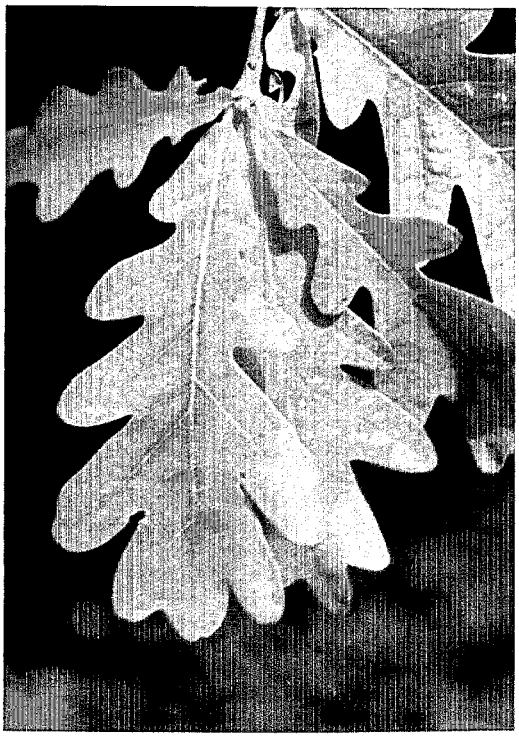

My 'Crimschmidt' variety has not been observed under all growing conditions and thus variations may occur as a result of different growning conditions. The following is a detailed description of my new variety of oak tree with color terminology in accordance with the Royal Horticultural Society Colour Chart (hereinafter RHS), published by The Royal Horticultural Society of London. The observations are of trees growing in Boring, Oreg.

Parentage: Exact parentage of pollen parent is unknown. The seed parent is *Quercus robur*.

Tree shape: Narrow, columnar tree with fastigiate branching.

Leaves: Alternate, simple, obovate with three to five pairs of rounded lobes. Leaves 9–18 cm long by 4 to 10 cm wide. Leaves are glabrous above and glabrous below except for scattered hairs along the veins on the underside. The leaf base is rounded to broadly acute.

Leaf color:

*Summer.*—Upper surface: RHS Green Group 136A to RHS Green Group 139A. Underside: RHS Green Group 138A.

*Fall.*—RHS Red Group 46A to RHS Greyed-Purple Group 183A.

Petioles: Stout, about 1 cm long.

Buds: Plump, rounded, 3–8 mm, with imbricate scales. RHS Greyed-Orange Group 175A to 175B.

Branches, mature 1 yr. growth: Small, glabrous, RHS Greyed-Purple Group 183A where exposed to sun, RHS Yellow-Green Group 148A on the shaded underside. Glaucous.

Bark: Smooth for the first three years, becoming furrowed in the fourth season. Lenticels 1–2 mm, oval to oblong. Color similar to RHS Greyed-Orange Group 165A.

Growth rate: Fast.

Flower and fruit: As no mature specimen of this new tree exists, flowers and fruit have not yet been observed.

Although the exact parentage of my new variety is unknown, my new variety is believed to be a hybrid seedling of *Quercus robur,* with *Quercus alba* being the probable pollen parent.

DISTINGUISHING CHARACTERISTICS

This new tree is understood to differ from the parent species (*Quercus robur*) as well as the upright form of the parent species (*Quercus robur* fastigiata) in the following ways:

| | New tree | *Quercus robur* |
|---|---|---|
| Leaf base: | rounded to broadly acute | auriculate |
| Fall color: | red or purple red | yellow-brown |
| Powdery mildew resistance: | demonstrated resistance | not believed resistant |

This new tree differs from *Quercus alba,* its possible pollen parent, in the following way:

| | New tree | *Quercus alba* |
|---|---|---|
| Form: | narrow, fastigiate | round |
| Leaf base: | rounded to broadly acute | cuneate |
| Growth rate: | fast | medium |

I claim:

1. A new and distinct variety of Oak tree substantially as herein shown and described, characterized particularly as to novelty by the combination of narrow fastigiate growth habit and red fall color.

* * * * *